United States Patent [19]

Bushman

[11] Patent Number: 5,543,917
[45] Date of Patent: Aug. 6, 1996

[54] OBJECT DETECTOR

[75] Inventor: Boyd B. Bushman, Lewisville, Tex.

[73] Assignee: Lockheed Martin Corporation, Fort Worth, Tex.

[21] Appl. No.: 329,338

[22] Filed: Oct. 26, 1994

[51] Int. Cl.[6] ............................................. G01J 4/00
[52] U.S. Cl. ........................ 356/364; 359/465; 359/501
[58] Field of Search .......................... 356/364–370; 250/225, 330, 342; 359/371, 386, 407, 483, 485, 501, 465

[56] References Cited

U.S. PATENT DOCUMENTS

| | | | |
|---|---|---|---|
| 3,904,293 | 9/1975 | Gee | 356/369 |
| 3,992,571 | 11/1976 | Garlick et al. | 356/365 |
| 5,138,162 | 8/1992 | Hacskaylo | |
| 5,264,916 | 11/1993 | Bushman | |
| 5,345,308 | 9/1994 | Bushman | |
| 5,404,225 | 4/1995 | Bushman | 356/364 |
| 5,452,089 | 9/1995 | Bushman | 356/364 |

*Primary Examiner*—Hoa Q. Pham
*Attorney, Agent, or Firm*—James E. Bradley

[57] ABSTRACT

A method for detecting objects while eliminating unwanted background utilizes polarizing contrasts. A lens systems focuses light from the field of view through a beam splitter. One beam passes to a digitizer through a polarizer which polarizes the beam at one angle. The other beam is reflected to another polarizer, which is located at a 90° angle relative to the first polarizer. The pixels from the polarized images are digitized. A processor compares the corresponding pixels, subtracting one from the other to find a polarizing contrast. A range that can be varied will display only those pixels which have polarizing contrasts within the selected range. The selection of the range will either include or eliminate the background while displaying man-made targets.

14 Claims, 2 Drawing Sheets

OBJECT DETECTOR

BACKGROUND OF THE INVENTION

1. Field of the Invention

This invention relates in general to detecting objects by detecting light reflections from an object, and in particular to a system that detects polarization contrast between two polarizing angles.

2. Description of the Prior Art

This invention deals with a method and apparatus for detecting objects, such as military targets. The targets may be trucks, tanks, artillery, aircraft, command centers and other systems. The targets may be protected by camouflage, foliage, or may be painted with a camouflage paint.

U.S. Pat. No. 5,264,916, Nov. 23, 1993 and U.S. Pat. No. 5,345,308, Sep. 6, 1994 show systems for detection using polarization. In those systems, the field of view is alternately polarized between two angles of polarization which are orthogonal to each other. Man-made objects, particularly those which have specular or shiny surfaces, exhibit flashing as the light polarizes from the first angle to the second angle. This flashing indicates to the observer that a man-made object is present within the field of view.

Sometimes military hardware will be hidden in shadows, under camouflage within trees and under embankments or bridges. Objects within shadows are more difficult to detect because sunlight does not impinge directly on them and the polarization contrast is not as great.

SUMMARY OF THE INVENTION

In this invention, the light from the field of view is polarized at a first angle of polarization to create a first image. This first image is digitized into a first set of pixels. Each of the pixels has an intensity value proportional to the light intensity reflected from objects within the field of view when polarized at the first angle. The light reflected from the same field of view, but which has not been polarized at the first angle of polarization, is digitized into a second set of pixels to create a second image. The pixels of the second set have intensity values proportional to the intensity of the light reflected from substantially the same field of view, but when not polarized at the first angle.

A processor determines the difference between the first and second sets of pixels by subtracting one from the other. A range is selected for comparing with the difference between each value. If the difference between the values for two corresponding pixels is within the range, then only that difference is displayed on a monitor. The range may be adjusted to have a low enough value such that the system will be able to discern differences in specular man-made objects that are located within shadows, or high enough to eliminate backgrounds and only detect tanks, trucks, and other targets of interest.

Preferably, the light which is digitized to create the second image is also polarized, but polarized at an angle that is orthogonal or 90 degrees to the first angle of polarization. Also, it is preferred to polarize the image with each of the polarizers simultaneously. In one embodiment this is handled by using a beam splitter. The light arrives simultaneously at the two polarizers after passing through the beam splitter. The digitizers are synchronized.

DETAILED DESCRIPTION OF THE INVENTION

Figure 1:
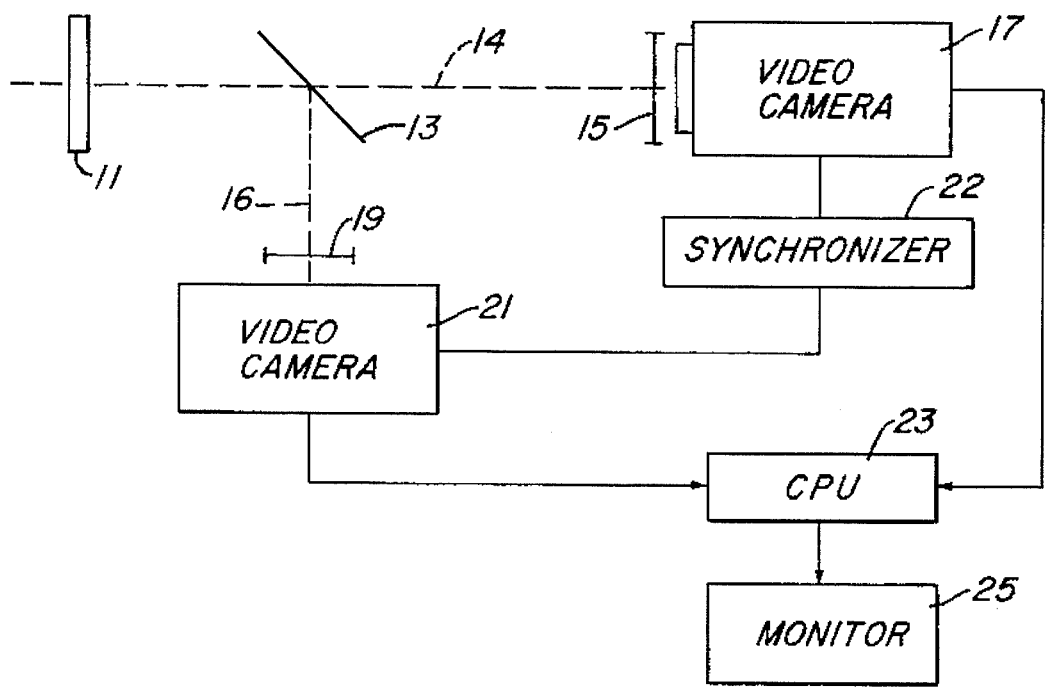
FIG. 1 is a schematic diagram illustrating an apparatus assembled in accordance with this invention.

Referring to FIG. 1, the apparatus of this invention has a lens array schematically indicated by the numeral 11. Light from the field of view passes through the lens array and impinges on a beam splitter 13. Beam splitter 13 is a conventional optical device which will pass one-half of the intensity of the light beam on a first path or beam 14 to a first polarizer 15. Beam splitter 13 causes another beam 16 to be directed 90 degrees to first beam 14.

Polarizer 15 is also a conventional optical device. A number of very fine lines (not shown) may be scribed or otherwise etched on the surface. Also, the polarizer 15 may be formed by chemical coating which aligns the molecules in parallel lines. The lines are extremely close and parallel to each other. The distance between the lines is less than the wavelength of light for which the polarizer 15 is designed. The lines are oriented in a particular direction, such as a horizontal direction. Polarizer 15 removes glare from light reflected from objects when the lines are oriented in a particular direction such as horizontal. This occurs as a result of light waves being unable to pass through the finely separated lines of the polarizer.

The beam 14 passing through polarizer 15 passes to a digitizing means which may be a conventional video camera 17. The image of beam 14 is digitized, pixel-by-pixel in a conventional fashion. Each pixel represents a part of the polarized image, with its value being representative of the intensity of the light of that particular portion of the object in view.

Beam splitter 13 directs second beam 16 at a 90° angle to the first beam 14 to a second polarizer 19. Polarizer 19 is identical to polarizer 15, however it is oriented with its lines orthogonal or 90° to those of polarizer 15. For example, if polarizer 15 is oriented horizontally, polarizer 19 will have its lines oriented vertically. The light passing through polarizer 19 passes to a second digitizing means, which is also a video camera 21 identical to video camera 17. Again, the image is electronically digitized into a large number of pixels, each pixel having a value representative of the intensity of a certain portion of the field of view.

Video cameras 17, 21 are controlled by a synchronizer 22 that synchronizes the digitizing process. As a particular pixel from first beam 14 is being digitized, the corresponding pixel from beam 16 is being simultaneously digitized. The corresponding pixels in beams 14 and 16 will differ from each other in intensity values only due to the effect of the polarizers 15, 19. The pixel values from video cameras 17, 21 pass to a central processing unit or computer 23 which processes this information and displays the information on monitor 25 in a manner which will be subsequently described. The polarizing and digitizing steps for beams 14, 16 are illustrated by the numerals 27 and 29 in the block diagram of FIG. 3.

Light beams 14, 16 are preferably visible light. The effect of polarization on visible light depends upon what the light is being reflected from. Specular man-made objects exhibit a greater polarizing contrast than natural objects. Most natural objects in the background will reflect light which varies little in intensity whether or not it is polarized, as indicated by the numeral 31 in FIG. 2. The visible light polarization contrasts for various materials in sunlight are shown, with the upper level for each material being observed through one of the polarizers 15, 17 and the lower level through the other of the polarizers 15, 17. Specular man-made objects, such as glass 33, have large polarization contrasts. The reflected energy varies approximately 23% whether the reflected light is polarized with polarizer 15 or polarizer 19. Paint, plastic and rubber, as indicated by the numeral 35, also exhibit a fairly strong polarizing contrast, but at a lower level than glass 33. For example, paint, plastic and rubber may exhibit a polarizing contrast from about 10 to 15% depending upon whether or not the light is polarized by polarizer 15 or polarizer 19. Metals 37 which are not shiny exhibit even a lower polarizing contrast, somewhat less than 10%. Background natural substances such as leaves, grass and soils exhibit a much lower polarizing contrast, as indicated by numeral 31.

Computer 23 is programmed to utilize the differences in polarizing contrast of various objects to display on the monitor only items which exhibit a polarizing contrast within a selected variable range. For example, glass, paint and metal objects located in shadows, such as highway overpasses and the like will not exhibit such a large polarizing contrast as in sunlight. Consequently, the software within computer 23 is configured to allow variability of the selected range to account for smaller variations in polarizing contrasts.

Figure 2:
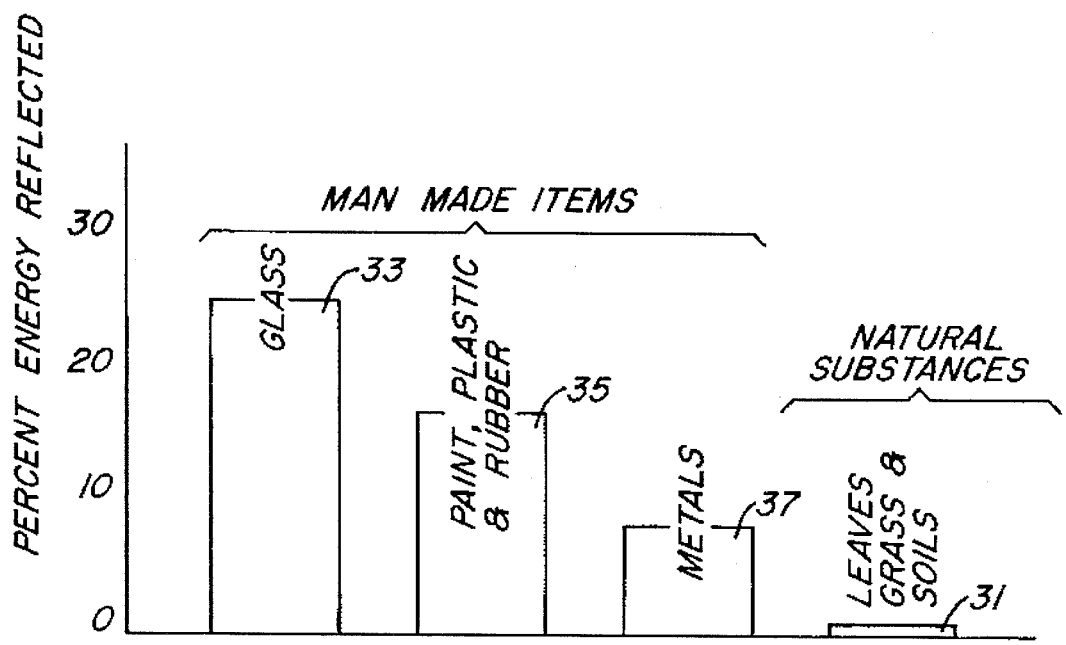
FIG. 2 is a graph showing a difference in intensities of energy reflected between first and second polarizing angles from various objects in sunlight.
Figure 3:
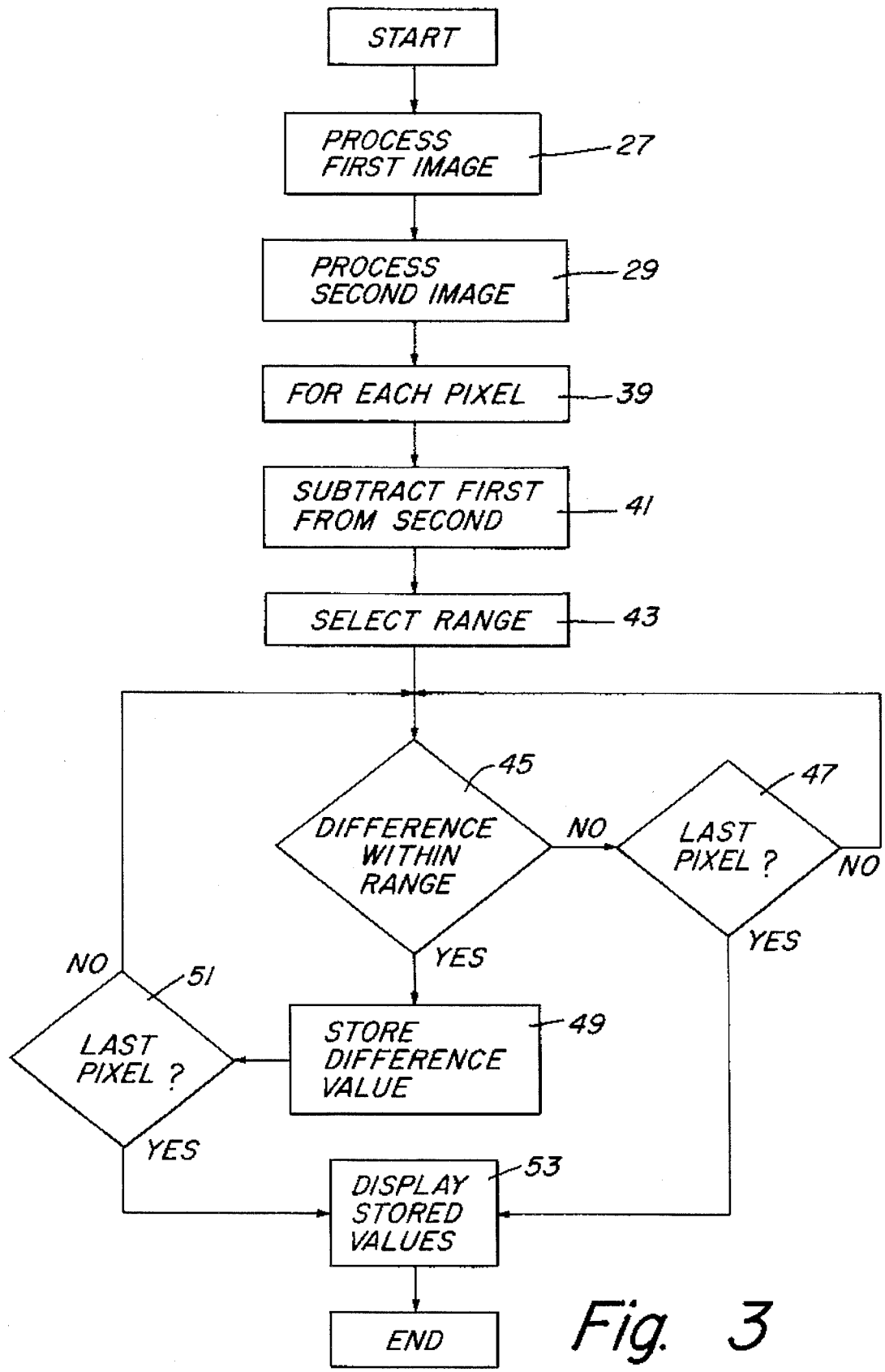
FIG. 3 is a flow chart illustrating the method of this invention.

Referring to FIG. 3, the detection process involves first processing the first image as indicated by step 27. That includes processing beam 14 as it passes through splitter 13. The first image is digitized into pixels. Step 29 indicates processing the second image or beam 16, which occurs simultaneously in the embodiment of FIG. 1. As indicated by steps 39 and 41, computer 23 subtracts the intensity values of one pixel from the other to find the difference. The difference in intensity value, or polarization contrast, could be as much as approximately 23 percent for glass in sunlight, as indicated by FIG. 2.

Step 43 indicates that a range of values for pixel polarization contrast is selected. A corresponding pixel from beam 14 and beam 16 will have a different value if it is part of a reflection from an object with a high polarizing contrast. This value eliminates natural backgrounds. In the preferred process, the apparatus of FIG. 1 will first scan a wide field of view, such as 30° to 40°. In this wide field of view, the selected range step 43 will normally be set at a fairly high level so that it will detect pixels which have high polarizing contrasts, such as more than 20% of the reflected energy. The selected range for the wide field of view may have a low threshold level, as well, but because of the high level, the contrast between pixels at the low level would not as likely be seen. For example, the range selected for the wide field of view may be each pixel that has a polarizing contrast between polarizer 15 and polarizer 19 that is between 5% and 25%. Background polarization contrasts will not be within this range, and the background 39 will be eliminated from the display on monitor 25. Glass 33 (FIG. 2), paint 35, and metals 37 may likely have a polarizing contrast within this range.

In step 45, the computer 23 determines whether or not the difference determined in step 41 is within the range selected in step 43. If not, step 47 inquires as to whether or not it was the last pixel. If not the last pixel, the process returns in an iterative fashion to step 45 and the next pixel is processed. If the polarizing contrast of the pixel from beams 14, 16 (FIG. 1) is within the selected range, that value is stored as indicated by step 49. Step 51 inquires as to whether or not that was the last pixel. If not, the computer 23 (FIG. 1) returns to step 45 in an iterative fashion and processes the next pixel difference. When all of the pixels of the particular frame are processed, the stored values are displayed as indicated in step 53. Only the stored values are displayed and these are the values that show a polarizing contrast within the selected range of step 43.

The select range step 43 will preferably be readily adjustable, such as by rotating a control knob. If the wide field of view indicates an object of interest, the operator may then actuate the lens system 11 (FIG. 1) to convert to a narrow, more highly magnified field of view in the area of interest. This narrow field of view may be of little as 1°–2°. The narrow field of view may be in a shadow area, such as under overpasses or like. When moving to the narrow field of view, the operator may also adjust the selected range. Typically, the operator would lower the upper threshold, because the polarizing contrast within the shadows will not be as high as shown in FIG. 2. The operator may also lower the lower threshold. For example, the range may be lowered from 2 to 5%. In this range, experiments have determined that man-made objects, particularly specular objects, will exhibit polarizing contrast even when in the shadows. This gives definition to objects otherwise not visible. For example, the darkened interiors of vehicles can be observed in the shadows by lowering the thresholds of the range sufficiently.

The invention has significant advantages. As the field of view is split into two beams of light, digitizing and subtracting the corresponding pixels occurs simultaneously. Consequently, the exact field of view is being compared between the two polarizing angles. For fast moving objects, such as airplanes flying at low altitudes, simultaneous processing is important. Also, when tracking objects that are moving fairly rapidly across a field of view, a simultaneous comparison between polarizing angles is important. The range selection step allows one to narrow a field of view and lower the polarizing contrast range to receive polarizing contrasts even within shadows. This is of assistance for analyzing objects that may be hidden under underpasses and under camouflage.

While the invention has been shown in only one of its forms, it should be apparent to those skilled in the art that it is not so limited, but is susceptible to various changes without departing from the scope of the invention.

I claim:

1. A method for searching for selected man-made objects within shadows, comprising:

(a) polarizing visible light reflected from a field of view at a first angle to create a first image;

(b) digitizing the first image into a first set of pixels, the first set of pixels having values proportional to the light reflected from objects within the field of view when polarized at the first angle;

(c) digitizing visible light reflected from substantially the same field of view, but which has not been polarized at the first angle, into a second set of pixels to create a second image, the second set of pixels having values proportional to the light reflected from substantially the same field of view when not polarized at the first angle; then (d) determining the difference in values of each of the first and second sets of pixels to determine a polarization contrast for each of the pixels of the first and second sets;

(e) selecting a range for the differences in values that has an upper level which substantially includes polarizing contrasts resulting from specular man-made objects located within shadows and a lower level which substantially excludes any polarizing contrasts resulting from natural background objects;

(f) determining if said difference in values are within the selected range; and, if so (g) displaying only said difference in values which are within the selected range on a monitor.

2. The method according to claim 1 wherein the light for steps (a) and (c) is received simultaneously.

3. The method according to claim 1 wherein in step (c), the light is also polarized, but at a second angle orthogonal to the first angle.

4. The method according to claim 1 wherein:

step (a) includes reducing the field of view if step (g) displays an object of interest, and step (e) includes lowering the upper level of the selected range; then the remaining steps are repeated.

5. A method for searching for selected man-made objects within shadows, comprising:

(a) polarizing visible light reflected from a field of view at a first angle to create a first image;

(b) digitizing the first image into a first set of pixels, the first set of pixels having values proportional to the light reflected from objects within the field of view when polarized at the first angle;

(c) simultaneously with step (a) polarizing visible light reflected from the same field of view at a second angle orthogonal to the first angle to create a second image;

(d) simultaneously with step (b) digitizing the second image into a second set of pixels, the second set of pixels having values proportional to the light reflected from the same field of view when polarized at the second angle; then (e) subtracting the values of the first set of pixels from the second set of pixels to determine a polarizing contrast for each of the pixels;

(f) selecting a range for the polarizing contrasts that has an upper level which substantially includes polarizing contrasts resulting from specular man-made objects located within shadows and a lower level which substantially excludes any polarizing contrasts resulting from natural background objects within the field of view;

(g) determining if the polarizing contrasts are within the selected range; and, if so (h) displaying only the polarizing contrasts which are within the range on a monitor.

6. The method according to claim 5 wherein steps (a) and (c) are performed by the following steps:

splitting the light from the field of view into first and second beams; and polarizing the first beam at the first angle; and polarizing the second beam at the second angle.

7. A method for searching for selected man-made objects, comprising:

providing a first polarizer which will polarize light at a first angle;

providing a second polarizer which will polarize light at a second angle orthogonal to the first angle;

receiving light reflected from a field of view and splitting the light received into a first beam and a second beam;

polarizing the first beam with the first polarizer to create a first image;

digitizing the first image into a first set of pixels, the first set of pixels having values proportional to the light reflected from objects within the field of view when polarized at the first angle;

polarizing the second beam with the second polarizer to create a second image;

digitizing the second image into a second set of pixels, the second set of pixels having values proportional to the light reflected from the same field of view when polarized at the second angle; then subtracting the values of the first set of pixels from the second sets of pixels to determine a polarizing contrast for each of the pixels;

selecting a range for the polarizing contrasts which has an upper level that substantially includes polarizing contrasts resulting from specular man-made objects located within shadows and a lower level which substantially excludes any polarizing contrasts resulting from natural background objects within the field of view;

determining if the polarizing contrasts are within the selected range; and, if so displaying only the polarizing contrasts which are within the range on a monitor.

8. The method according to claim 7 wherein the light received is visible light.

9. An apparatus for searching for selected man-made objects within shadows, comprising:

polarizing means for polarizing visible light reflected from a field of view at a first angle to create a first image;

first digitizing means for digitizing the first image into a first set of pixels, the first set of pixels having values proportional to the light reflected from objects within the field of view when polarized at the first angle;

second digitizing means for digitizing visible light reflected from substantially the same field of view, but which has not been polarized at the first angle, into a second set of pixels to create a second image, the second set of pixels having values proportional to the light reflected from substantially the same field of view when not polarized at the first angle;

means for selecting a range for the difference between the values of the first and second sets of pixels that has an upper level which substantially includes those resulting from specular man-made objects located within shadows and a lower level which substantially excludes any differences between the values of the first and second sets of pixels due to natural background objects; and comparison means for subtracting the values of the first set of pixels from the second sets of pixels to determine a difference for each of the pixels, and if said differences are within the range, for displaying only those differences that are within the range on a monitor.

10. The apparatus according to claim 9 wherein the polarizing means polarizes light for the first image and the second image simultaneously.

11. The apparatus according to claim 9 wherein the light digitized by the second digitizing means is also polarized, but at a second angle, orthogonal to the first angle.

12. The apparatus according to claim 9 wherein the polarizing means comprises:

means for splitting the light from the field of view into first and second beams;

a first polarizer for polarizing the first beam at the first angle; and a second polarizer for polarizing the second beam at a second angle which is orthogonal to the first angle.

13. An apparatus for searching for selected man-made objects, comprising in combination:

a beam splitter for receiving light reflected from a field of view and splitting the light received into a first beam and a second beam;

a first polarizer which will polarize the first beam at a first angle;

a second polarizer which will polarize the second beam at a second angle orthogonal to the first angle;

first digitizing means for digitizing the first image into a first set of pixels, the first set of pixels having values proportional to the light reflected from objects within the field of view when polarized at the first angle;

a second digitizing means for digitizing the second image into a second set of pixels, the second set of pixels having values proportional to the light reflected from the same field of view when polarized at the second angle;

means for selecting a range for the difference between the values of the first and second sets of pixels that has an upper level which substantially includes those resulting from specular man-made objects located within shadows and a lower level which substantially excludes any differences between the values of the first and second sets of pixels due to natural background objects; and means for subtracting the values of the first set of pixels from the second sets of pixels to determine a difference, and if said differences are within the selected range, displaying only said differences which are within the range on a monitor.

14. The apparatus according to claim 13 wherein the first and second polarizers polarize visible light.

\* \* \* \* \*